United States Patent [19]

Hanson et al.

[11] Patent Number: 4,776,042
[45] Date of Patent: Oct. 11, 1988

[54] CRYOKENETIC HEADBAND

[76] Inventors: Oliver D. Hanson, 2225 Viking Blvd., NW., Cedar, Minn. 55011; Donald R. Nicolai, P.O. Box 415, Monticello, Minn. 55362

[21] Appl. No.: 85,639

[22] Filed: Aug. 13, 1987

[51] Int. Cl.⁴ ............................................. A42B 1/24
[52] U.S. Cl. ............................................. 2/7; 2/171; 2/DIG. 11; 2/199; 383/901
[58] Field of Search ............ 2/7, 171.2, 171.3, 185 R, 2/199, 422, DIG. 11, 171; 383/901

[56] References Cited

U.S. PATENT DOCUMENTS

| 115,894 | 6/1871 | Prevot | 2/7 |
| 1,434,854 | 11/1922 | Stall | 2/171 |
| 2,335,630 | 11/1943 | Bachardy | 2/7 |
| 3,159,160 | 12/1964 | Ullom | 2/171.2 X |
| 4,130,902 | 12/1978 | Mackenroth et al. | 2/7 |
| 4,277,847 | 7/1981 | Florio | 2/12 |
| 4,551,858 | 11/1985 | Pasternack | 2/7 |

Primary Examiner—Peter Nerbun
Attorney, Agent, or Firm—Orrin M. Haugen; Thomas J. Nikolai; Frederick W. Niebuhr

[57] ABSTRACT

A cryokenetic headband having a closable pocket for retaining a cold pack material is disclosed. The headband is intended to be worn during exercise or work to keep the head cool and perspiration from running into the wearers eyes.

4 Claims, 1 Drawing Sheet

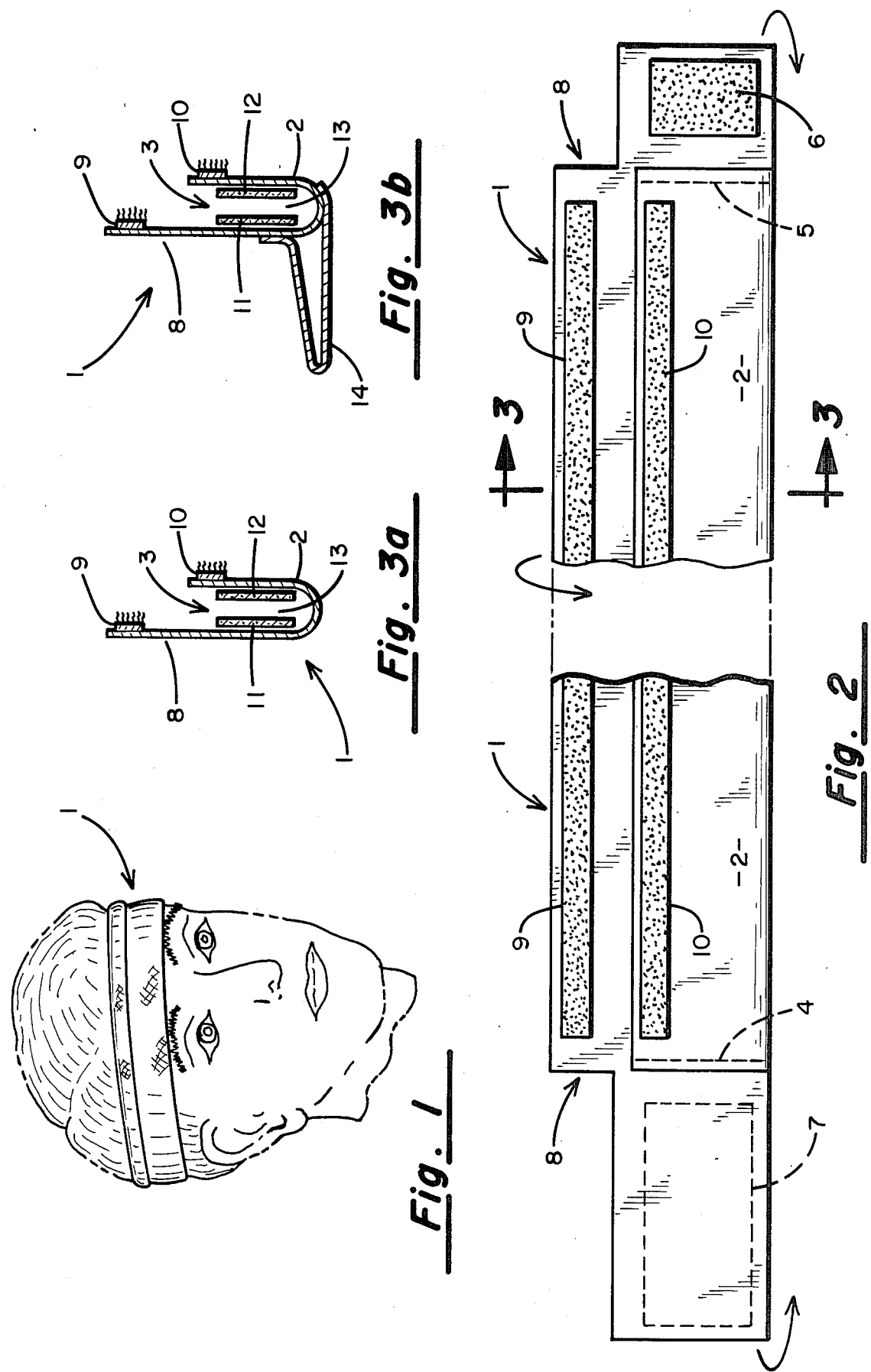

CRYOKENETIC HEADBAND

BACKGROUND OF THE INVENTION

1. Field of the Present Invention

The present invention relates to a cryokenetic headband which is intended to be used during heavy work or exercise. More particularly, the present invention relates to cryokenetic headband which is intended to surround the head of the wearer above the eyes and incorporates a pocket suitable for containing a cold pack material.

2. Discussion of the Prior Art

As those skilled in the art will immediately recognize, sweatbands intended to absorb sweat from the brow of the wearers head have been available for many years. These bands essentially reduce the occurrence of sweat dripping into the wearers eyes and causing a painful stinging sensation. Similarly, those involved in heavy work or strenuous exercise have found that considerable relief from the heat can be achieved by holding a pack of ice to the forehead or pouring cool water over the head. Missing from the prior art, however, is a relatively inexpensive versatile headband which permits cold pack materials such as crushed ice to be contained therein.

SUMMARY OF THE INVENTION

The headband of the present invention is constructed of a porous, absorbent material that includes a pocket into which a variety of cold pack materials can be placed. In one embodiment, the pocket has a flap hook and loop type closure typically sold under the Velcro name. The closure permits the pocket to be opened and closed for insertion and retention of cold pack materials such as crushed ice. In a second embodiment, the permanent cold retaining material is placed in the pocket and the flap is stitched closed. The cold retaining material is chilled by placing the headband in a refrigerator or freezer. The cold retaining material can alternatively be chilled by submersing the headband in cold or iced water, then squeezing excess water to a correcting volume desired by the wearer.

OBJECTS

A primary object of the present invention is to provide a headband having a pocket into which cold pack materials can be placed.

Another object of the invention is to provide such a headband which is adjustable to fit heads of varying sizes.

Still another object of the present invention is to provide a headband which can be comfortably worn and has a cold pack containing pocket.

This and other objects of the invention will become more clear from a reading of the detailed description of the preferred embodiment set forth below.

BRIEF DESCRIPTION OF THE DRAWINGS

FIG. 1 shows the headband of the present invention as its intended to be worn.

FIG. 2 is a plain view of the headband of the present invention in its fully open position.

FIG. 3a is a cross-section of the headband of FIG. 2 through line 3—3.

FIG. 3b is a cross-section of the headband similar to but which further includes an optional visor.

DETAILED DESCRIPTION OF THE PREFERRED EMBODIMENT

As shown in the figures, the cyrokenetic headband 1 of the present invention is intended to wrap around the head of the wearer in the area of the forehead. It is comprised of an elongated strip of porous cloth material 2. We have found that terry cloth is a suitable material for the band but other absorbent materials may be used as well. A key feature of the present invention is a pocket 3 formed in the band 1. In order to form the pocket 3, the elongated strip of material 2 has been folded over as shown in FIGS. 3a and 3b. The folded over material is then stitched (4 and 5) to retain the shape of the pocket 3.

Associated with the opposite ends and opposite sides of the elongated strip 2 are the respective hook member 6 and loop member 7 of a closure of the type sold under the Velcro trademark. As those skilled in the art will recognize, members 6 and 7 can be secured to the strip material in a number of acceptable ways such as adhesive or stitching. This closure comprised of hook and loop members 6 and 7 permits the band to be adjustably secured around the head.

Another important feature of the present invention is the flap 8 which is intended to be folded over to close the pocket 3. In one embodiment, a hook and loop type closure comprised of members 9 and 10 is present to retain the flap in its closed position.

With the pocket 3 and the flap 8 so formed, the apparatus permits the insertion of two elongated, highly absorbent sponges or pads 11 and 12 into the pocket. A cold packing material such as crushed ice can then be inserted in the pocket in the space 13 between the two elongated pads 11 and 12. The flap member 8 is folded over to close the pocket and closure members 9 and 10 retain the flap member 8 in its closed position sealing the cooling material inside the pocket 3.

Alternatively, a cold retaining material can be placed into the pocket 3 and the flap 8 can then be stitched closed to permanently seal the cold pack material within the pocket 3. Said cold pack material can be any one of a variety of cooling agents. The only requirements for said cooling agents are that they are either a solid phase substance, or if a liquid or gaseous substance, packaged or wrapped so that they will not flow through the porous material of the headband. The cold retaining material can also be chilled in a variety of ways including placing the headband in a refrigerator or freezer or in a container filled with cold or iced water.

An optional feature of the headband of the present invention is the addition of a sun visor 14 shown in FIG. 3b. This sun visor is preferably made of a stiff, yet absorbent material which is attached to the elongated strip material 2. Not only does visor 14 help keep the sun out of the wearers eyes, but also keeps water from the melting of the ice or perspiration from draining into the eyes.

While the invention has been disclosed by reference to the details of a preferred embodiment thereof, it is to be understood that the disclosure is intended to be in an illustrative rather than a limiting sense, and it is contemplated that various modifications in a finished article will readily occur to those skilled in the art, that or within the spirit of the invention within the scope of the appended claims.

I claim:

1. A cryokenetic headband comprising a porous cloth strip having means associated with opposite ends thereof for adjustably securing said opposite ends together to form a band, said band having a pocket formed along the length thereof for retaining cold pack materials, a pair of sponge pads sized to be insertable within said pocket on opposite sides of said cold pack material, a flap coextensive with said pocket, and means associated with said flap for sealing the pocket.

2. The apparatus of claim 1 further including a visor secured to said porous cloth strip.

3. The apparatus of claim 1 wherein said means for adjustably securing opposite ends of the porous cloth strip together is a hook and loop type closure.

4. The apparatus of claim 1 wherein said closure means for sealing the pocket is a hook and loop type closure.

* * * * *